United States Patent
Han et al.

(10) Patent No.: US 11,654,227 B1
(45) Date of Patent: May 23, 2023

(54) WET SEAL SUCTION DEVICE

(71) Applicants: Sang In Han, Fairview Heights, IL (US); Eugene Han, Redding, CT (US); Rebecca Han, Oak Park, IL (US)

(72) Inventors: Sang In Han, Fairview Heights, IL (US); Eugene Han, Redding, CT (US); Rebecca Han, Oak Park, IL (US)

(*) Notice: Subject to any disclaimer, the term of this patent is extended or adjusted under 35 U.S.C. 154(b) by 271 days.

(21) Appl. No.: 16/905,968

(22) Filed: Jun. 19, 2020

Related U.S. Application Data (60) Provisional application No. 62/864,138, filed on Jun. 20, 2019.

(51) Int. Cl.
| | | |
|---|---|---|
| *A61M 1/00* | (2006.01) | |
| *A61B 17/24* | (2006.01) | |
| *A61B 90/30* | (2016.01) | |

(52) U.S. Cl.
CPC .......... *A61M 1/7411* (2021.05); *A61B 17/24* (2013.01); *A61B 90/30* (2016.02); *A61B 2017/246* (2013.01); *A61B 2217/005* (2013.01); *A61M 2205/587* (2013.01); *A61M 2210/0618* (2013.01); *A61M 2210/0662* (2013.01)

(58) Field of Classification Search
CPC .......... A61M 1/7411; A61M 2205/587; A61M 2210/0618; A61M 2210/0662; A61B 17/24; A61B 90/30; A61B 2017/246; A61B 2217/005

See application file for complete search history.

(56) References Cited

U.S. PATENT DOCUMENTS

| | | | |
|---|---|---|---|
| 16,136 | A | 11/1856 | Watson |
| 290,961 | A | 12/1883 | Bixby |
| 4,468,216 | A * | 8/1984 | Muto ..................... A61M 1/85 604/43 |
| 4,828,546 | A | 5/1989 | McNeil |
| 4,930,997 | A | 6/1990 | Bennett |
| 5,368,017 | A * | 11/1994 | Sorenson .......... A61M 16/0858 128/207.14 |
| 5,562,077 | A * | 10/1996 | Schultz ............. A61M 16/0463 128/207.14 |
| 5,730,727 | A * | 3/1998 | Russo ................. A61M 1/7411 604/118 |

(Continued)

FOREIGN PATENT DOCUMENTS

| | | |
|---|---|---|
| EP | 2124766 B1 | 6/2013 |
| JP | 5208961 B2 | 4/2010 |
| JP | 2013536050 A | 9/2013 |

*Primary Examiner* — Susan S Su
*Assistant Examiner* — Eric Rassavong
(74) *Attorney, Agent, or Firm* — Leason Ellis LLP (57) ABSTRACT

A suction device that incorporates liquid to form a wet seal with a foreign body and/or debris, enabling an effective contact for extraction from canals, passages, and other bodily areas of a patient. A liquid chamber is formed between a distal nozzle and a distal end of a main body. The liquid chamber acts as a reservoir to facilitate a wet seal at the distal end of the embodiment. A vacuum provides suction through the embodiment, and a pressure release outlet is incorporated into the main body to allow for variation of suction force, affecting the moisture coverage presented to the area of extraction. Nozzle tip attachments may be affixed to the distal nozzle to further facilitate foreign body extraction. Other embodiments are described and shown.

17 Claims, 7 Drawing Sheets

(56) References Cited

U.S. PATENT DOCUMENTS

| | | | |
|---|---|---|---|
| 5,902,314 A | 5/1999 | Koch | |
| 5,916,150 A | 6/1999 | Sillman | |
| 5,928,218 A * | 7/1999 | Gelbfish | A61B 17/320783 |
| | | | 604/164.11 |
| 7,802,574 B2 | 9/2010 | Schulz | |
| 8,012,141 B2 | 9/2011 | Wright | |
| 9,117,202 B2 | 8/2015 | Huttner | |
| 9,119,744 B2 | 9/2015 | Wellen | |
| 9,427,504 B2 * | 8/2016 | Newman, Jr. | A61M 1/76 |
| 2006/0167469 A1 * | 7/2006 | Arden | A61M 1/84 |
| | | | 606/109 |
| 2006/0287656 A1 | 12/2006 | Brown | |
| 2010/0010435 A1 * | 1/2010 | McCrary | A61M 1/7411 |
| | | | 604/73 |
| 2010/0042122 A1 | 2/2010 | Shar, Jr. | |
| 2012/0078059 A1 * | 3/2012 | Perez-Cruet | A61B 17/0218 |
| | | | 600/210 |
| 2014/0005490 A1 * | 1/2014 | Vayser | A61B 1/0625 |
| | | | 600/249 |
| 2014/0100584 A1 * | 4/2014 | Konstorum | A61B 17/3468 |
| | | | 606/109 |
| 2016/0157873 A1 * | 6/2016 | Griffin | A61B 17/22 |
| | | | 606/127 |
| 2017/0112980 A1 * | 4/2017 | Purnell | A61M 1/0001 |

* cited by examiner

WET SEAL SUCTION DEVICE

CROSS REFERENCE TO RELATED APPLICATIONS

This application claims the benefit of provisional patent application Ser. No. 62/864,138, filed 2019 Jun. 20 by the present inventor, which is incorporated by reference in its entirety.

FIELD OF INVENTION

The invention relates generally to medical suction devices and more particularly to hand-held aspirating devices that are used to extract foreign bodies from various bodily areas of a patient.

BACKGROUND OF THE INVENTION

Foreign bodies regularly become lodged within bodily canals, orifices, passages, cavities, and other hard to reach areas of a patient. They often arrive as a result of accidental insertion, by play, or intentionally. Blockages of bodily canals are commonly caused by objects such as beads, nuts, small parts of toys, pebbles, popcorn kernels, food, insects, and other small bodies. Those affected may experience a range of reactions, from mild discomfort to panic in instances such as if breathing or hearing becomes affected. Sometimes the removal of a foreign body requires minimal effort, while other times more deliberate methods of extraction are required. In these latter cases, the suffering individual may be taken to the hospital or clinic so that a caretaker can extract any lodged objects.

There are currently several methods used in medical practice to remove foreign bodies from a patient, but nevertheless all the existing methods and tools heretofore known exhibit a number of disadvantages. For example, tools such as forceps, cerumen loops, curettes, and hooks often involve methods that include scraping, scooping, and grasping. These methods may incur trauma to the sensitive linings of bodily passages, which can lead to discomfort, swelling, and bleeding. Additionally, these tools are often used in conditions that lack clear visualization, thereby increasing the risk of further damage to the affected bodily areas.

Other extraction techniques include the use of adhesives to glue a foreign body to an instrument, which may complicate the extraction process if glues make contact with bodily tissues. Other devices such as a speculum or a balloon-tip catheter require a flexible bodily canal such as that of the nose, and so their application is not ideal for more ridged passages such as the ear canal. With regard to problematic foreign bodies, the removal of those with a smooth surface, such as a bead or popcorn kernel, can be difficult as a reliable contact with an extraction device may be difficult to achieve.

Ad hoc solutions include the use of a cut section of flexible tubing which is then attached to a vacuum or catheter apparatus. This method may present the operator with an uneven distal tip to grasp the foreign body, thereby reducing chances of a clean contact, and reducing the success of extraction. Likewise, in such ad hoc solutions, the section of flexible tubing may prove too soft for precise handling within the bodily canal.

SUMMARY OF THE INVENTION

Accordingly, the present invention is directed to improved hand-held medical devices for the extraction of foreign bodies, and related methods of use, which obviate one or more of the limitations and disadvantages of the prior art. Devices according to the invention improve the quality and possibility of the contact between a foreign body and the device itself by using a wet seal for contact, thereby limiting suction air leakage, and so improving the conditions for successful extraction. Thus, devices of the invention perform substantially better than current apparatuses, and are prone to less trauma to the patient than current methods.

In accordance with one embodiment a device is attached to a suction source, and comprises a conduit with an integrated pressure release outlet, and an attached nozzle with an integrated liquid chamber. This chamber acts as a reservoir in which liquid can backflow out of the device in a controlled manner using said pressure release outlet, providing for a liquid-assisted, or wet, seal with a foreign body. The rate of backflow is determined by an operator's control of the pressure release outlet. In one embodiment, a flow stopper within the nozzle chamber acts to manage the rate of backflow. Once extraction of a foreign body is achieved, the devices according to the invention may be returned to the affected area of the patient for further aspirating of debris and general cleaning.

Accordingly, several advantages of one or more aspects are as follows: to provide extraction of foreign bodies from bodily canals, passages, crevices, and other areas, that causes minimal to no perceivable trauma to the affected bodily tissues, that does not require access to the back-facing side of the foreign body where visualization is limited, that does not require adhesives that may incur further trauma to the canal, that does not require construction from rigid or sharp materials which can easily damage the lining of bodily canals, and that which can grasp a foreign body with a smooth facing surface. Other advantages of one or more aspects will be apparent from a consideration of the drawings and forthcoming descriptions.

It is to be understood that both the foregoing general description and the following detailed description are exemplary and explanatory only and are not restrictive of the invention, as claimed.

DRAWINGS—REFERENCE NUMERALS

101 main body
102 distal nozzle 104 pressure release outlet
106 LED 108 battery release tab
110 stepped tube diameters 112 negative pressure source
114 battery cover 115 optional nozzle tip attachment
203 nozzle conduit
216 flow stopper 218 liquid chamber
220 friction ridges 222 blockage prevention channels
324 LED pins 326 battery
428 suction channel 430 release conduit
532 release outlet flange
734 battery housing 736 battery release tab channel
940 optional nozzle tip attachment
942 optional nozzle tip attachments (long)
944 optional nozzle tip attachments (short)
1346 liquid source
1648 wet seal
1650 example foreign body for extraction

DESCRIPTION OF THE EMBODIMENTS

Description will now be made in detail to the present exemplary embodiments of the device illustrated in the accompanying drawings. Wherever possible, the same last two numbers will be used throughout the drawings to refer to the same or like parts, whereas numbers preceding the last two will reference the associated figure number. When referring to a suction device that is manipulated by a caretaker or operator in order to aspirate a site, passage, cavity, or canal, the terms "proximal" and "distal" may be used to describe the relation or orientation of the device with respect to the operator as it is used. Therefore, the term "proximal" will be used to describe a relation or orientation of the device that, when in use, is positioned toward the operator (i.e., at the handle or base end of the device), and the term "distal" will be used to describe a position or orientation of the device that, when in use, is positioned away from the operator (i.e., at the other end of the device, such as the nozzle, towards which the embodiment will make contact with the foreign body to be extracted and/or dislodged). The terms aural and otic are used interchangeably herein when used as descriptors, referring to elements related to the ear (e.g., otic canal refers to the ear canal).

Although the disclosure hereof is detailed and exact to enable those skilled in the art to practice the invention, the physical embodiments herein disclosed merely exemplify the invention which may be embodied in other specific structures. While the preferred embodiments have been described in relation to use at bodily canals for the extraction of foreign bodies, the details may be changed without departing from the invention, which is defined by the claims. Still, it should be appreciated that the devices and methods that embody features of the preferred embodiment are also adaptable for use at any bodily site or canal where extraction may be beneficial.

The devices and methods are particularly well suited for extracting foreign bodies from aural and nasal passages due to a wide variety of possible causes. For this reason, the devices and methods will be described in this context. Still, it should be appreciated that the disclosed devices and methods are applicable for use in treating other symptoms elsewhere in the body, which are not necessarily nasal or aural related.

Figure 1:
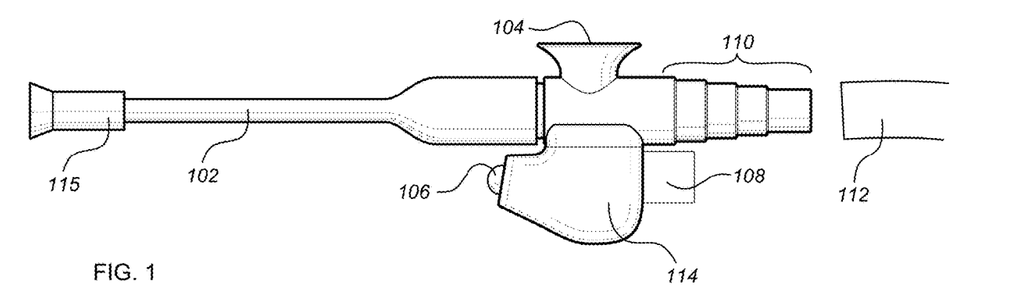
FIG. 1 is a side view of a medical device with indication of a suction hose to the right, according to an embodiment of the present disclosure.

One embodiment of the aspirator is illustrated in FIG. 1 (side view). In one embodiment, a distal nozzle 102 is attached to the distal end of a main body 101, which can be held together by friction and whose connection can be aided by friction ridges 220. However, this attachment can be achieved by any other method such as negative suction, or a physical connection such as a clip, threading, or pin connection. A negative pressure source 112, such as a hose with suction pressure, is connected to the proximal end of the main body. Their connection is aided by stepped tube diameters 110, to accommodate for a range of suction hose sizes and materials. In one embodiment, the distal nozzle 102 is a flexible plastic, such as polyethylene (PE). The main body 101 is made of polycarbonate, but can be composed of any material that can maintain its form while attached to a suction source, such as polypropylene, polystyrene, vinyl, nylon, stainless steel, etc.

Figure 4:
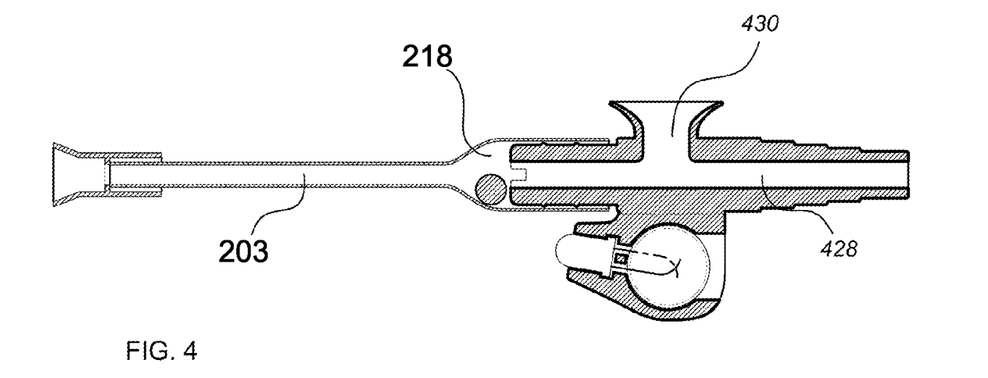
FIG. 4 is a cross-section view of a medical device, illustrating a suction channel that extends from the embodiment's proximal end (right) to its distal end (left), according to an embodiment of the present disclosure.
Figure 5:
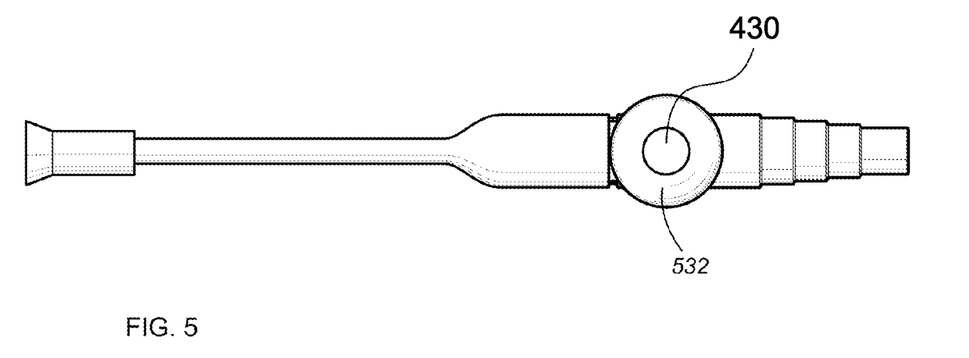
FIG. 5 is a top view of a medical device with a pressure release outlet facing the viewing angle, according to an embodiment of the present disclosure.

The main body measures roughly 55 mm in length, 35 mm in height, and 20 mm in width. In one embodiment, the main body has a pressure release outlet 104 along its top orientation (FIG. 1), within which a release conduit 430 connects to a suction channel 428 formed along the length of the main body (FIG. 4). In other embodiments, the release outlet may be positioned along different orientations, and may protrude from the main body at different heights, or no height at all. The pressure release outlet can be shaped with a release outlet flange 532 to accommodate for covering the release outlet (FIGS. 5 and 6), with a finger or any other obstruction to cover a pressure release outlet 104.

Figure 6:
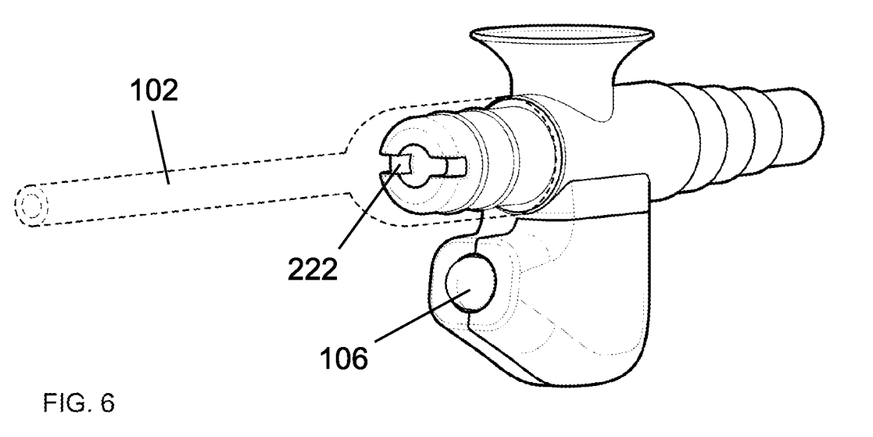
FIG. 6 is an angled side view of a medical device with a distal nozzle partially outlined, according to an embodiment of the present disclosure.
Figure 7:
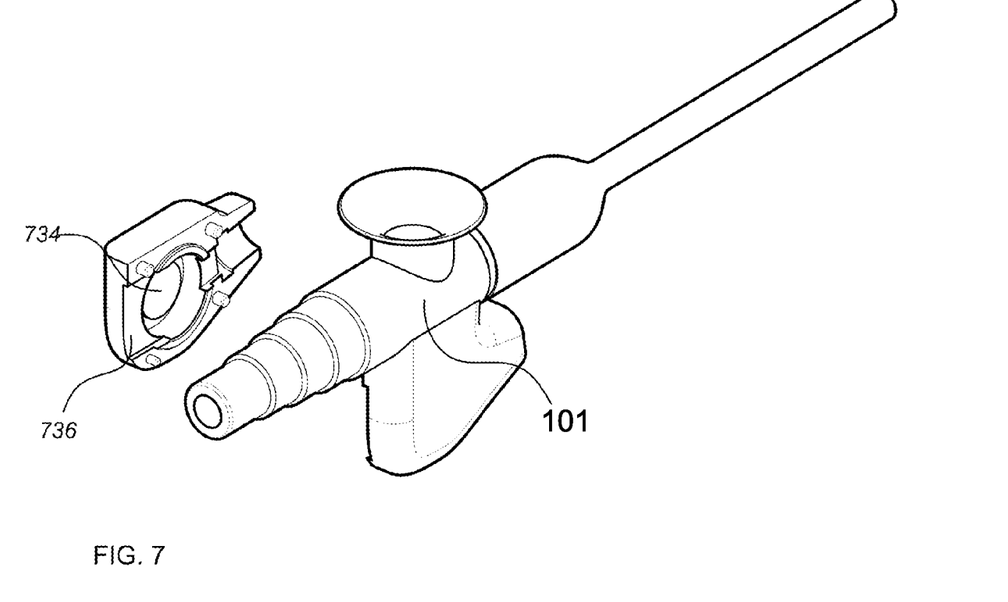
FIG. 7 is a perspective view of a medical device with a battery cover partially removed to indicate its interior, according to an embodiment of the present disclosure.
Figure 8:
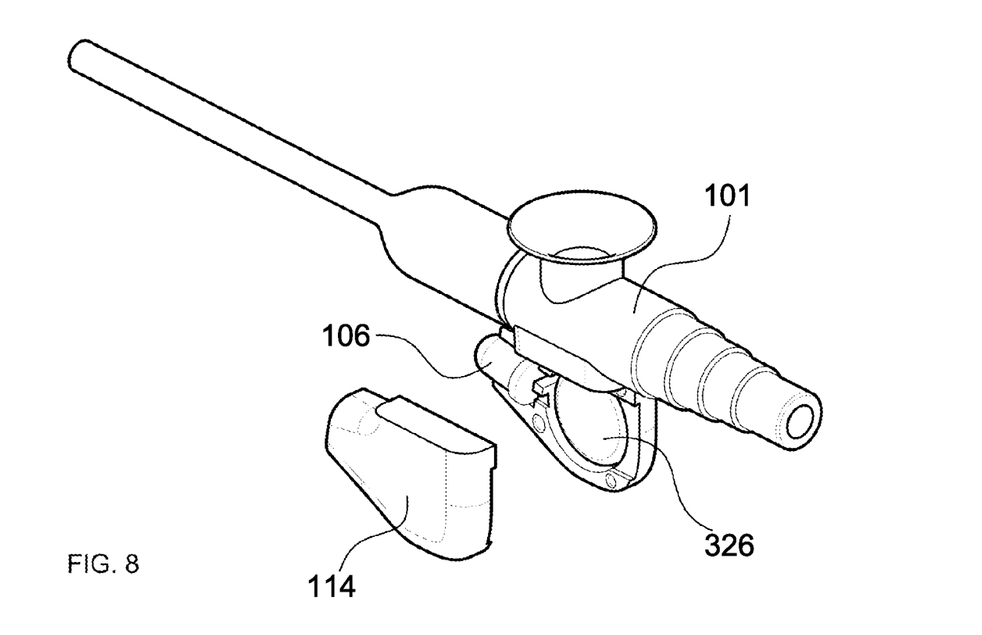
FIG. 8 is another perspective view of a medical device with a battery cover partially removed to indicate a battery and LED housing at the bottom half of the device, according to an embodiment of the present disclosure.

Blockage prevention channels 222 (FIG. 2) are notched within the distal extremity of the main body, facing a liquid chamber 218. FIG. 6 shows a perspective view of the blockage prevention channels 222, which are typically hidden by the distal nozzle 102. The shape of these channels may take on other forms, including perforations, a mesh, or notches of any geometric profile, such that air and liquid can pass through the liquid chamber 218 into the suction channel 428. A light-emitting diode (LED) 106 is attached to the bottom of the main body, and is oriented towards the direction of the distal nozzle, so as to illuminate the area of the foreign body extraction. The LED is wired to batteries 326 (FIG. 3) within a battery housing 734 (FIG. 7). A battery release tab 108 is placed between the batteries, and protrudes from the main body across a battery release tab channel 736. The LED, the batteries, and the battery release tab are held together to the main body with an affixed battery cover 814 (FIG. 8). In one embodiment, the battery cover is adhered using permanent adhesives, however, it may also be affixed using a snapping, clipping, or other securing mechanism to the main body.

Figure 2:
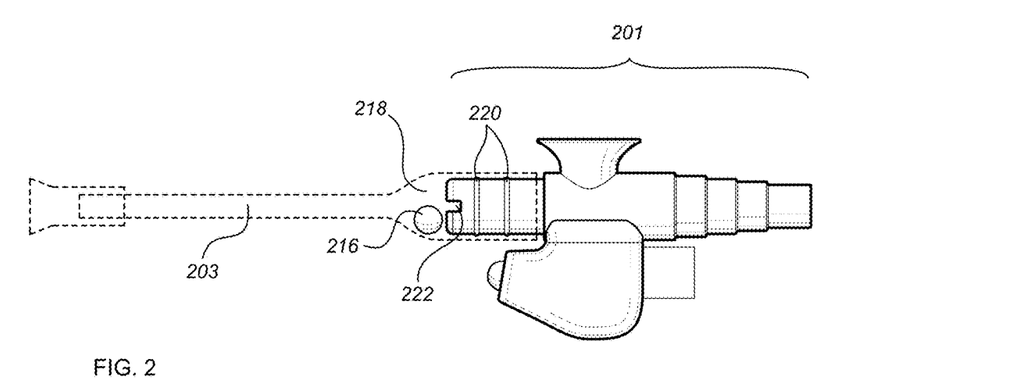
FIG. 2 is a side view of a medical device with a distal nozzle partially outlined to reveal internal components within a nozzle chamber, according to an embodiment of the present disclosure.
Figure 3:
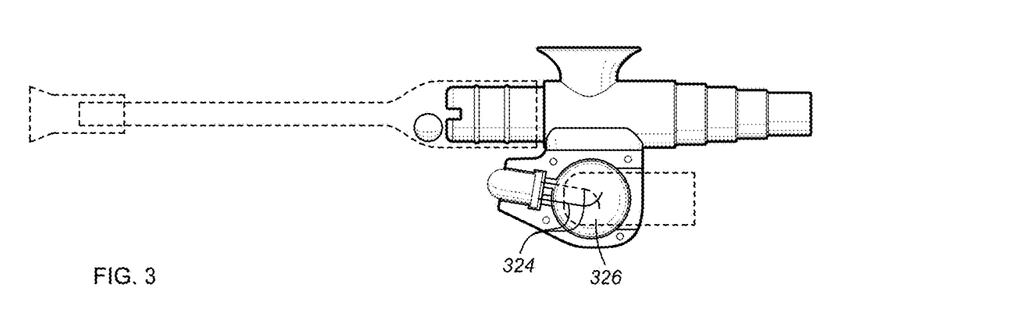
FIG. 3 is a side view of a medical device with the distal insertion tip partially outlined and a battery cover removed to illustrate an assembly of the battery and LED housing structure, according to an embodiment of the present disclosure.

The nozzle attaches to the distal end of the main body, measuring roughly 70 mm in length. Its distal diameter opening may have a range of sizes to accommodate for a variety of bodily features, such as from 2 mm-8 mm. The liquid chamber 218 is created between the nozzle and the main body (FIG. 2), which acts as a reservoir for liquid to be housed during operation. Within this chamber is a flow stopper 216 (FIG. 2). In one embodiment, the flow stopper is in the shape of a ball, however, it may take on any other form in which a one-way valve prevents back flowing, either partially or fully, from the liquid chamber towards the distal end of the nozzle. Other embodiments include one-way flaps, conical stoppers, or sponges that inhibit flow in one direction. In one embodiment, the flow stopper 216 is composed of a stainless-steel ball, however, it can be composed of other materials including plastics, other metals, glass, rubber, etc.

Figure 9:
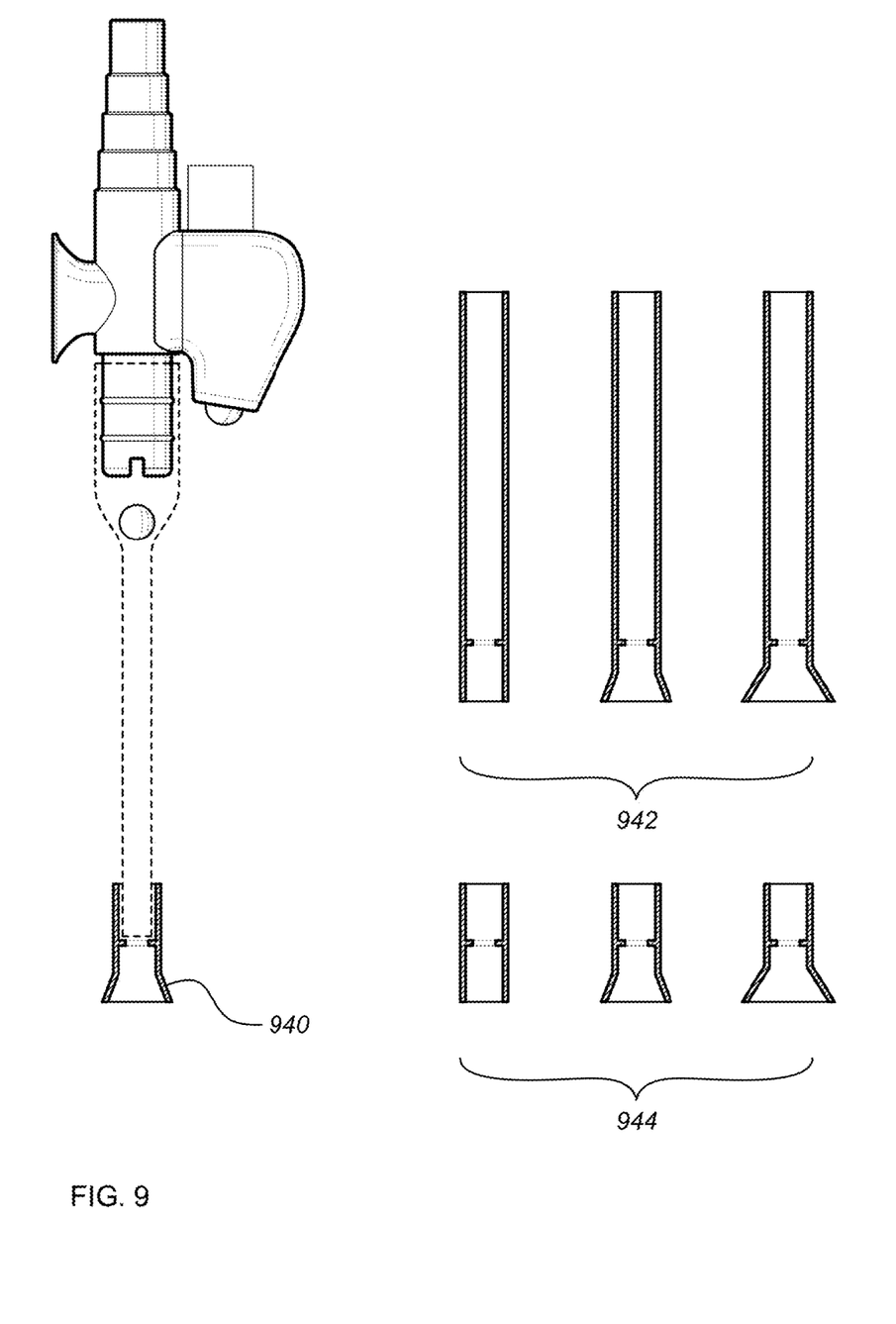
FIG. 9 illustrates cross-sectional side views of various nozzle tip embodiments that can accommodate for a range of distal tip sizes and shapes, according to an embodiment of the present disclosure.

A variety of nozzle tip attachments 940, 942, and 944 can be attached to the distal end of the distal nozzle 102 (FIG. 9). In one embodiment, connection between the nozzle and a nozzle tip attachment is achieved through friction, although this can be done using other forms of connection, such as with a threaded connection or other locking mechanisms. Nozzle tip attachments can be either flexible or rigid, depending on the suitability of application. For flexible tip attachments, they can be manufactured from soft plastics, silicone, rubber, etc. Rigid tip attachments can be made from plastics, glass, metals, rubber, etc. Nozzle tip attachments 940, 942, and 944 may exhibit a range of shapes and features, such as flanged, straight, smooth, brushed, ribbed, short, long, conical, cylindrical, bulbous, perforated, etc., to accommodate for various of applications, bodily areas, or foreign body materials and shapes.

Figure 10:
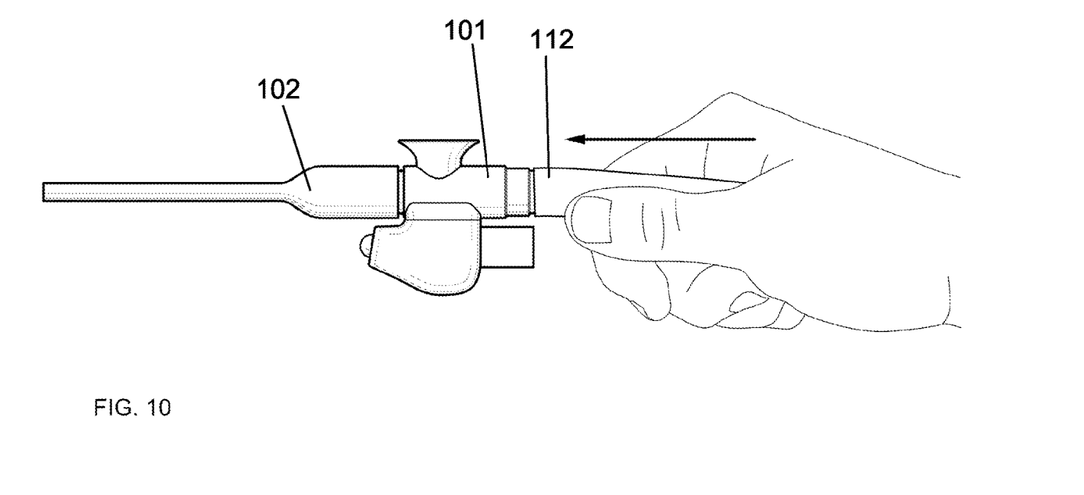
FIG. 10 is a side view of a medical device showing the process of connecting a suction hose to the proximal end of the embodiment, according to an embodiment of the present disclosure.

As illustrated in FIG. 10, a physician, caretaker, or other relevant operator, attaches a suction hose 112 from a vacuum source onto the device's proximal end, which is formed by a series of stepped tube diameters 110 to ensure a tight fit using a variety of hose sizes. The source of the vacuum may come from a variety of apparatuses, most commonly including central vacuum systems that are permanently installed within health care facilities and hospitals, as well as to mobile vacuum apparatuses. At the distal end of the embodiment, a semi-flexible nozzle 102 is attached to the device's main body 101 with raised surface ribs 220 for secure attachment.

Figure 11:
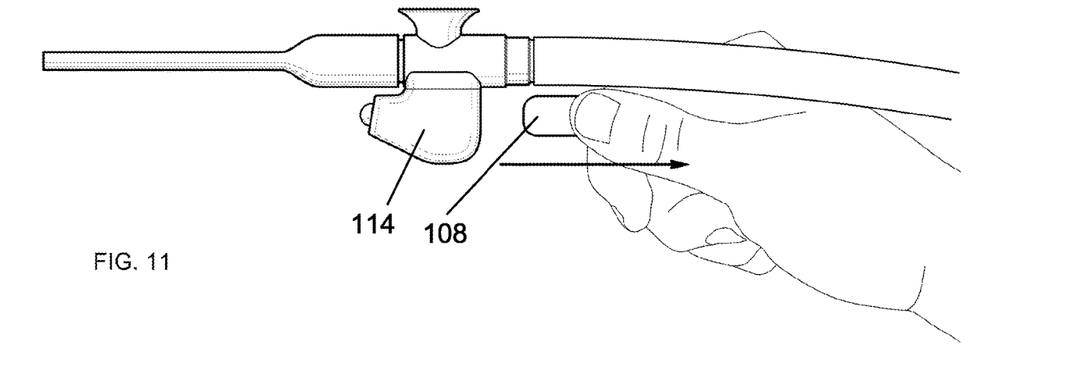
FIG. 11 is a side view of a medical device showing the process of removing a battery release tab to turn on an integrated LED, according to an embodiment of the present disclosure.

An LED 106 is attached to the underside of the main body 101, which illuminates the area of extraction, by pulling out a battery release tab 108, as illustrated in FIG. 11. Removal of the battery release tab 108 allows completion of an electrical circuit through the battery source 326, supplying electricity to the LED 106. The removal of the battery release tab 108 is facilitated by a battery release tab channel 736 (FIG. 7).

Figure 13:
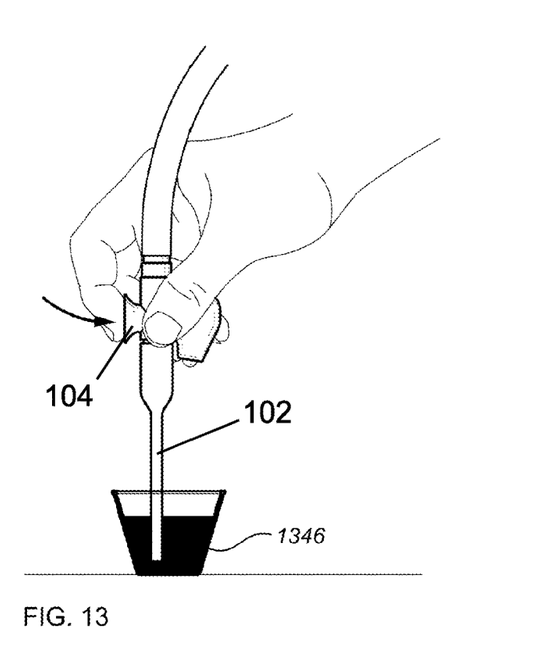
FIG. 13 is a side view showing introduction of a medical device into a vessel of liquid, and coverage of a top pressure release outlet, according to an embodiment of the present disclosure.

By covering the pressure release outlet 104 either partially or fully with a finger or other form of obstruction (FIG. 13), the force of suction is adjusted through a suction channel 428. The release outlet flange 532 facilitates coverage using an operator's finger over a bell-shaped surface.

Figure 12:
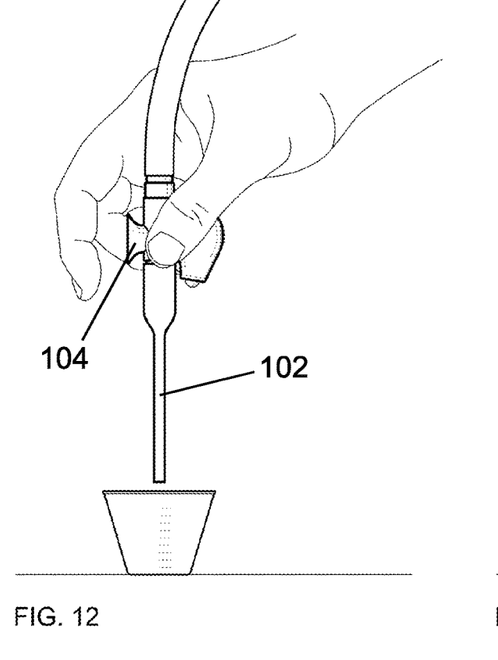
FIG. 12 is a side view of a medical device illustrating preparation for use above a vessel containing liquid, according to an embodiment of the present disclosure.
Figure 14:
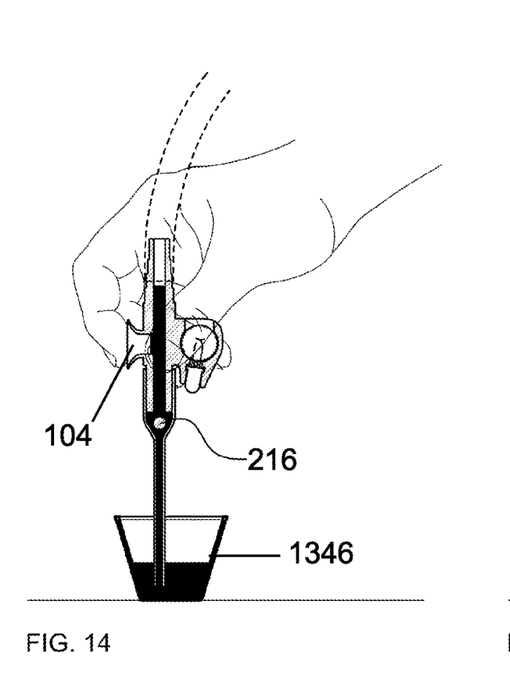
FIG. 14 is a cross-sectional side view showing a process of initial liquid suction by submerging a distal nozzle of a medical device into a vessel of liquid, and either partially or fully covering a top pressure release outlet, according to an embodiment of the present disclosure.
Figure 15:
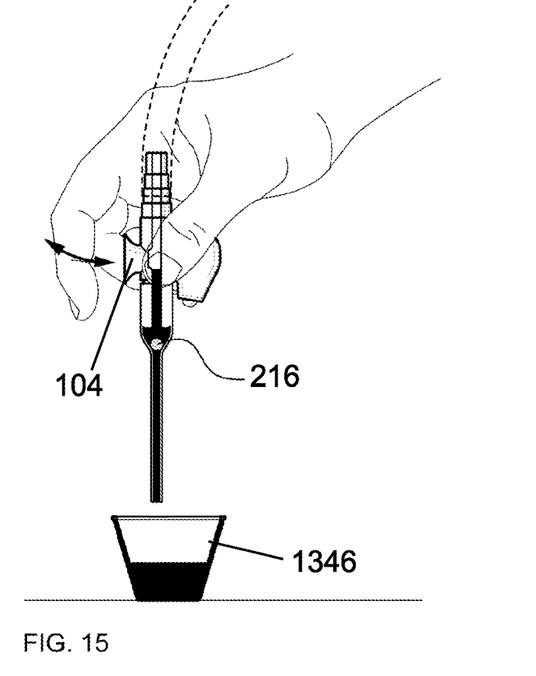
FIG. 15 is a cross-sectional side view showing a process of adjusting the amount of liquid drawn into a liquid chamber of a medical device, according to an embodiment of the present disclosure.

After a negative pressure source is attached to the device, the operator then prepares liquid (e.g. such as water, mineral oil, etc.) in a vessel, as illustrated in FIG. 12. To draw in liquid into the device's liquid chamber 218, the operator introduces the device's distal nozzle into the prepared liquid vessel, adjusting the amount of coverage over the pressure release outlet 104 to control the rate of liquid suction through the device's suction channel 428. As shown in FIG. 14, a flow stopper 216 is housed within the liquid chamber 218, which acts as a one-way valve, allowing liquid to enter through the suction channel 428. As indicated in FIG. 15, the more that the pressure release outlet 104 is covered, the stronger the overall suctional force of the device, forcing a higher rate of flow through the device. Conversely, when the operator lifts or slides their finger and uncovers the pressure release outlet 104, suctional force is reduced, and a partial amount of liquid flows back out from the device's distal end. However, the flow stopper 216 inhibits the complete drainage of liquid from the liquid chamber 218. Blockage prevention channels 222 prevent the flow stopper 216 from entirely blocking suction through to the suction channel 428. The operator may adjust the amount of liquid intake by adjusting the coverage of the release conduit 430 with their finger.

Figures 16, 17:
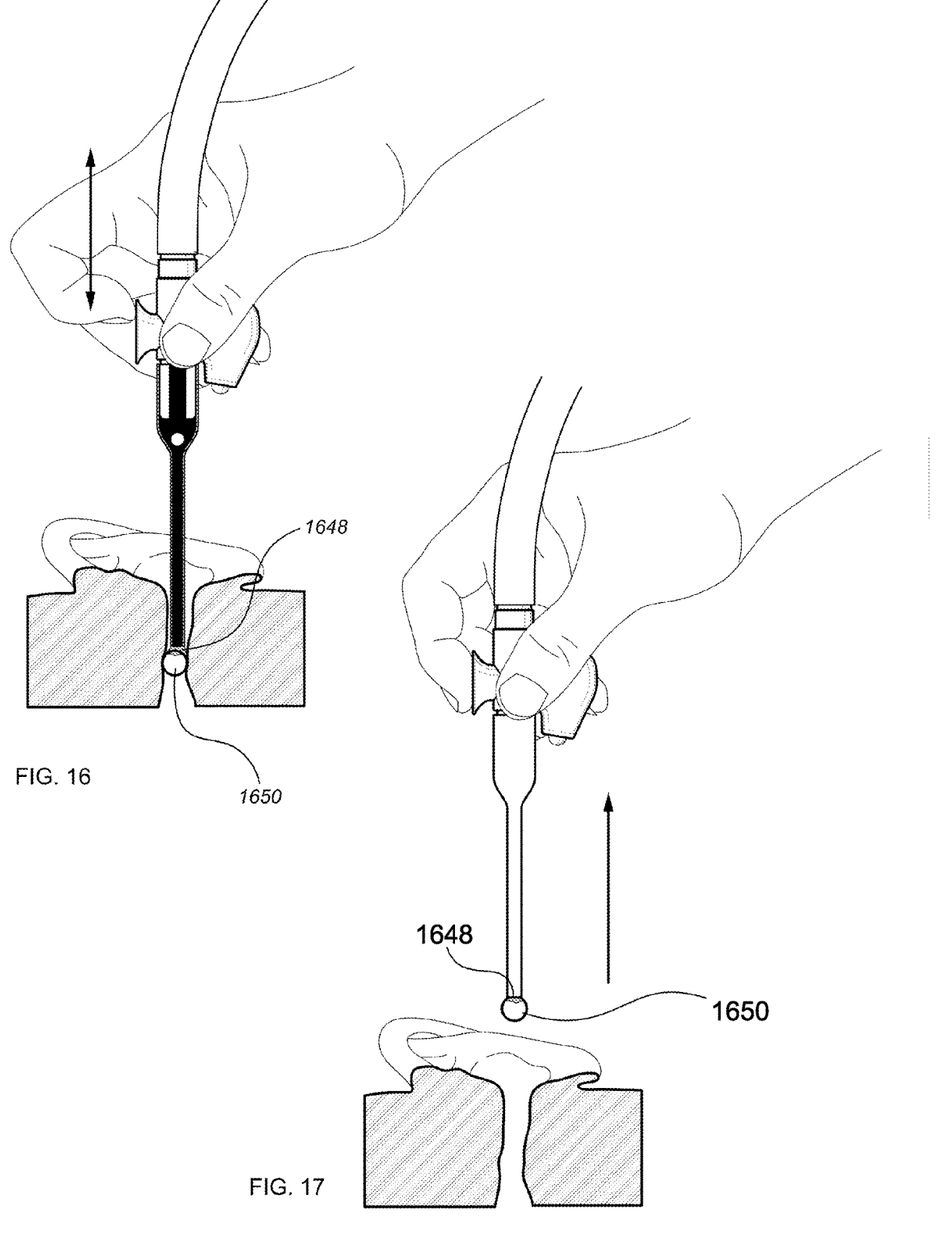
FIG. 16 is a cross-sectional side view illustrating the insertion of a medical device into an ear canal to establish initial contact with a foreign body, according to an embodiment of the present disclosure.
FIG. 17 is a cross-sectional side view indicating the process of foreign body extraction from an ear canal, according to an embodiment of the present disclosure.

Once the desired amount of liquid is presented in the liquid chamber 218, the device is now properly prepared for aspirating with a wet seal. The operator now locates the foreign body to be removed within the canal, orifice, or other affected area of the patient. As shown in FIG. 16, the operator initiates the extraction process by contacting a foreign body 1650 with the distal nozzle 102. Liquid that is present towards the distal end of a nozzle conduit 203 will form a liquid wet seal 1648, which improves suction efficacy by discouraging air leaks that may be present in an otherwise dry suction. If the liquid wet seal 1648 is lost or its quantity is reduced below the desired level, the operator may alter the size of the available opening of the pressure release outlet 104 by sliding their finger across the release outlet flange 532. As the operator uncovers the aperture of the release conduit 430, suctional force in the nozzle 102 is reduced, and liquid within both the nozzle conduit 203 and the liquid chamber 218 is encouraged to backflow out of the distal end of the device. This backflow provides liquid to reinitiate a liquid-facilitated wet seal 1648.

When a wet seal has been made between the distal nozzle 102 and a foreign body 1650, the operator can pull away or otherwise maneuver the device from the affected body part of the patient, thereby extracting the foreign body, as shown in FIG. 17. To further clean out the affected area of the patient, the operator may return the distal nozzle 102 to the area of extraction, and use the device as an aspirator, cleaning out any debris and remaining material that was encountered and/or resulted from the original extraction process. Both during extraction of a foreign body 1650 as well as during clean up after extraction, the operator may attach a range of nozzle tip attachments 940, 942, and 944 to the distal end of the nozzle 102 to facilitate extraction and/or clean up procedures.

While our above description contains many specificities, these should not be construed as limitations on the scope, but rather as an exemplification of one embodiment thereof. Many other variations are possible. Accordingly, the scope should be determined not by the embodiment illustrated, but by the appended claims and their legal equivalents. For example, while the preferred embodiment illustrates a rigid plastic nozzle tip attachment 940, variations include a number of materials such as glass, metal, synthetic composites, etc. Variations may thus be composed of a range of material characteristics, such as rigid, flexible, semi-flexible, rubbery, smooth, sticky, etc. As well, the material characteristics of alternative embodiments for nozzle tip attachments may be transparent, translucent, or opaque, to facilitate visualization during use.

In the preferred embodiment, the LED 106 is positioned towards the bottom of the main body, aimed toward the distal end of the nozzle to illuminate the area of foreign body extraction. In alternative embodiments, the LED 106 may be located elsewhere along the device, such as towards the sides or on top of the main body, and may also be located such that its illumination is contained within the distal nozzle 102 itself. For example, the wall of the distal nozzle 102 can be constructed from a material with a refractive index that allows light to "bounce" along and through the nozzle, thereby illuminating outwards towards the direction of the foreign body to be extracted.

Likewise, while the preferred embodiment illustrates an integrated LED 106, alternative embodiments may include a modular lighting source that can be attached independently on the device. Additionally, alternative embodiments may also include variations that do not include any lighting source.

A flow stopper 216 is located within the liquid chamber 218, working as a partial one-way valve in which liquid can flow freely into the liquid chamber 218, however said flow stopper 216 discourages backflow out of the nozzle 102. Alternative embodiments may include variations of the flow stopper 216, such as a flap, a sponge, a valve, or any such variation in which liquid is readily passed towards the proximal end of the device, yet partially or fully blocked when flowing towards the distal end of the device.

In the preferred embodiment, liquid 1346 is vacuumed into the liquid chamber 218 from a separate liquid vessel. However, in alternative embodiments, said liquid may be automatically fed into the device through a continuous feeding system, such as an integrated water line.

The distal nozzle 102 can be made larger or smaller in size, longer or shorter in length, and wider or narrower in tip diameter to accommodate for a variety of applications, such as suitability for fitting within various bodily passages, accommodating for different reservoir volumes, to modulate overall negative pressure, manufacturing efficacy, etc.

While the preferred embodiment attaches a distal nozzle 102 with a main body 101 as two separate objects, alternative embodiments may include designs for a device made of a single part integrating both nozzle and main body functions. Similarly, while the preferred embodiment includes a distal nozzle 102 and optional nozzle tip attachments 940, 942, and 944 as separate elements, in alternative embodiments, they may be integrated as a single element.

From the description above, a number of advantages of some embodiments of our wet-seal suction device become evident:
(a) The incorporation of a wet-seal suction enables a firm and reliable contact between the distal tip of the embodiment and the foreign object to be removed.
(b) The use of suction reduces the risk of trauma to the patient's bodily canals as it forgoes any scraping, mechanical grasping, and accidental contact with adhesives.
(c) Multiple attempts at removal are innocuous, as irritation to the inner lining of bodily canals is minimal, whereas repeated attempts with devices that scrape, scoop, or gouge, increases the chances of physical harm to the patient.
(d) At minimum, a user of the embodiment would require a only single hand for operation, whereas devices such as forceps, curettes, speculums, etc. may require the use of multiple hands for successful foreign body removal.

Thus the reader will see that at least one embodiment of the medical device provides a convenient and versatile suction device that can be used by operators to extract foreign bodies from affected bodily areas, by establishing a secure contact between the device and the foreign body using a liquid-assisted, or wet, seal. The device is suited to a variety of affected bodily areas of a patient, including but not limited to, otic canals, nasal canals, orifices, crevices, passages, etc. Furthermore, a variety of materials and shapes for nozzle tip attachments allows use of the device in a range of bodily aspects, as well as for a multitude of foreign body types and contours.

Variations, modifications, and other implementations of what is described herein will occur to those of ordinary skill in the art without departing from the spirit and the scope of the invention as claimed. Accordingly, the invention is to be defined not by the preceding illustrative description but instead by the spirit and scope of the following claims.

Having described our invention, what we claim is:

1. A medical suction device comprising:
a main body being composed of a rigid material, the main body having a suction channel formed therein, the main body having a distal end and a proximal end for connection to a vacuum source, the suction channel having an open distal end and a proximal end for connection to the vacuum source;
a detachably attaching distal nozzle being mounted on the distal end of said main body, the distal nozzle being composed of a semi-flexible material,
wherein said distal nozzle is configured to make contact with a foreign body or debris for extraction from a surgical field;
wherein said distal nozzle includes a distal end and an opposite proximal end for connection to the main body, the nozzle comprising a nozzle conduit terminating at an open distal end and having a proximal end that fluidly communicates with the suction channel of the main body, wherein the distal nozzle has a liquid chamber defined therein at the proximal end that acts as a reservoir for liquid, the liquid chamber being located distal to the distal end of the main body; and
a movable flow stopper that is disposed within the liquid chamber distal to the distal end of the main body and is configured to allow flow of the liquid in a proximal direction towards the suction channel, while restricting flow in a distal direction within the nozzle conduit.

2. The main body of claim 1, further comprising a hole in communication with the suction channel that can be opened and closed by a user's finger to control the suction at the distal end of said device.

3. The suction device of claim 1, further including a light emitting diode (LED) attached to said device.

4. The suction device of claim 3, further including an electrical source to supply electricity to said LED.

5. The suction device of claim 1, further including a detachably attaching nozzle tip attachment.

6. Wherein said nozzle tip attachment of claim 5, being mounted on the distal end of said nozzle.

7. The suction device of claim 1, wherein said main body material is polycarbonate, acrylic, or other plastics.

8. The suction device of claim 1, wherein said nozzle material is polyethylene, polycarbonates, or other plastics.

9. The suction device of claim 1, wherein a proximal end portion of the distal nozzle is enlarged relative to a center and distal end portion of the distal nozzle, the proximal end portion defining the liquid chamber that contains the movable flow stopper.

10. The suction device of claim 1, wherein the distal end of the main body includes a plurality of blockage prevent channels in the form of notches formed in and being open at the distal end of the main body.

11. The suction device of claim 10, wherein the plurality of blockage channels are in fluid communication with the open distal end of the suction channel and are configured to permit air and liquid to flow into the suction channel even if the flow stopper obstructs the open distal end of the suction channel.

12. The suction device of claim 2, wherein the main body includes a distal end portion over which the distal nozzle is disposed and held in place, the distal end portion being located distal to the hole.

13. The suction device of claim 9, wherein the flow stopper comprises a ball valve that is unable to enter the center of the distal nozzle and unable to enter the distal end of the main body.

14. A medical suction device comprising:
 a main body being composed of a rigid material, the main body having a suction channel formed therein, the main body having a distal end and a proximal end for connection to a vacuum source, the suction channel having an open distal end and a proximal end for connection to the vacuum source, the main body having a lower extension that extends along a bottom of the main body below the suction channel, the lower extension terminating in a distal end;
 a detachably attaching distal nozzle being mounted on a distal end of said main body, the distal nozzle being composed of a semi-flexible material, wherein said distal nozzle is configured to make contact with a foreign body or debris for extraction from a surgical field;
 wherein said distal nozzle includes a distal end and an opposite proximal end for connection to the main body, the nozzle comprising a nozzle conduit terminating at an open distal end and having a proximal end that fluidly communicates with the suction channel of the main body, wherein the distal nozzle has a liquid chamber defined therein at the proximal end that acts as a reservoir for liquid, the liquid chamber being located distal to the distal end of the main body; and
 a light emitting diode (LED) disposed along the distal end of the lower extension and being oriented to project light in a distal direction toward the distal end of the distal nozzle.

15. The suction device of claim 14, wherein the lower extension defines a battery housing in which a battery is contained, the battery being operatively connected to the LED.

16. The suction device of claim 14, wherein the lower extension and the main body are formed integral to one another and comprise a single molded part.

17. A method of engaging and extracting a foreign object by suction with the aid of a liquid comprising the step of:
 providing the medical suction device of claim 1;
 connecting the proximal end of the main body to the vacuum source;
 introducing the distal end of the distal nozzle within a source of the liquid;
 actuating the vacuum source such that liquid from the liquid source is drawn into the distal nozzle and is collected in the liquid chamber;
 introducing the distal nozzle into a surgical field;
 establishing moisture along an area of contact between the distal nozzle and the foreign body;
 adjusting a quantity of the moisture between the distal nozzle and the foreign body by opening and closing a hole in the main body, that is in communication with the suction channel, with a user's thumb or finger, affecting a volume of the liquid within the liquid chamber;
 using suction that is facilitated by the moisture at the distal end of the distal nozzle to engage and retain the foreign body at the distal end of the distal nozzle; and
 withdrawing the medical suction device from the surgical field.

* * * * *